Nov. 15, 1960 D. H. MOREY, JR Plant Pat. 1,984
ROSE PLANT
Filed Jan. 28, 1960
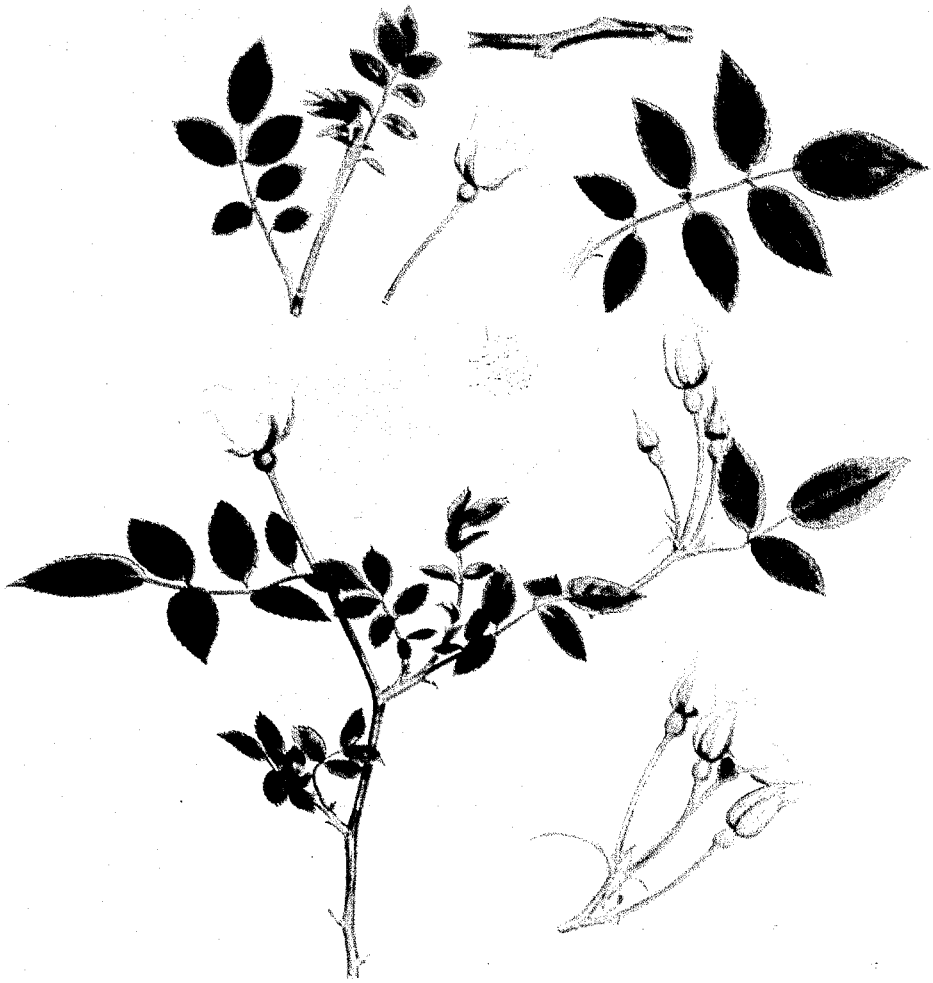
INVENTOR
D. H. Morey, Jr.
BY Robb & Robb
ATTORNEYS United States Patent Office Plant Pat. 1,984
Patented Nov. 15, 1960

1,984

ROSE PLANT

Dennison H. Morey, Jr., Pleasanton, Calif., assignor to Jackson & Perkins Company, Newark, N.Y., a corporation of New York Filed Jan. 28, 1960, Ser. No. 5,326

1 Claim. (Cl. 47—61)

The present invention relates to a new and distinct variety of rose plant of the miniature class, which was originated by me by crossing the variety "Cecile Brunner" (unpatented) with the variety "Rosy Jewel" (Plant Patent No. 1,899).

The primary objective of this breeding was to produce a new rose variety of the smaller Minima type having some of the characteristics of the variety "Cecile Brunner." This objective was achieved by virtue of the fact that both the color and flower form of the parent variety "Cecile Brunner" have been carried forward into the new variety which is the subject hereof and, in addition, other desirable improvements have been attained in my new miniature rose, as evidenced by the following characteristics which are outstanding in the new variety and which distinguish it from its parents, as well as from all other varieties of which I am aware:

(1) A flowering formation similar to the blooming habit of the parent variety "Cecile Brunner," which usually bears three or four buds together;

(2) A miniature form of the flowers which average approximately ¾" in diameter;

(3) A distinctive pink color shading of the buds which may be generally described as Venetian Pink; and (4) A distinctive La France Pink general color tonality of the flowers.

Asexual reproduction of the new variety by own-rooted cutting, as performed at Pleasanton, California, and also at Newark, New York, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Cecile Brunner."
*Pollen parent.*—"Rosy Jewel."

*Flower*

(Observations made from specimens grown outdoors at Newark, New York, near mid-afternoon in the latter part of the month of July.)

Blooming habit: Recurrent—continuous.
Bud:
*Size.*—Small.
*Form.*—Ovoid; is not affected by wet or hot weather.
*Color.*—When sepals first divide—Sea-Foam Yellow, Plate 31. When petals begin to unfurl—Marguerite Yellow, Plate 30, lightly overcast with Thulite Pink, Plate 26. When half-blown: inside of petals—Ivory Yellow, Plate 30, lightly overcast with Venetian Pink Plate 13; reverse of petals—Marguerite Yellow, Plate 30, with edges of petals lightly overcast with Cameo Pink, Plate 26.
*Sepals.*—Slightly branched; curl back when petals begin to unfurl. Color: inside—Absinthe Green, Plate 31; outside—Light Bice Green, Plate 17.
*Calyx.* — Color — Light Bice Green, Plate 17. Shape — pear. Size — small. Aspect — smooth. Odor when rubbed—none.
*Peduncle.* — Length — short. Aspect — smooth. Strength—erect; slender. Color—Biscay Green, Plate 17.
*Opening.*—Opens up well; is not affected by adverse weather conditions.
Bloom:
*Size.*—Small. Average size when fully expanded—from ¾" to 1".
*Borne.*—Several together.
*Stems.*—Short; strong.
*Form (when first open).*—Cupped. Permanence—retains its form to the end, but outer petals curl back.
*Petalage.*—Double (full but open center). Number of petals under normal conditions—20.
*Color.*—Center of flower—La France Pink, Plate 1. Outer petals—upper half of petal Hermosa Pink, Plate 1, and lower half of petal White, Plate 53. Base of petals (aiglet)—Pale Chalcedony Yellow, Plate 17. Inside of petals—White, Plate 53, lightly overcast with La France Pink, Plate 1. Reverse of petals—White, Plate 53, lightly overcast with Cameo Pink, Plate 26. General tonality from a distance—La France Pink, Plate 1.
*Discoloration.*—General tonality at end of first day—La France Pink, Plate 1. Second day—White, Plate 53, lightly overcast with La France Pink, Plate 1. Third day—White, Plate 53, lightly overcast with Hermosa Pink, Plate 1.
Petals:
*Texture.*—Thin; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; few; regularly arranged around styles. Color—Light Orange-Yellow, Plate 3.
Stamens, filaments (threads); Short. Color—Maize Yellow, Plate 4.
Pollen: Color—Pale Yellow-Orange, Plate 3.
Styles: Bunched; uneven length; short; thin.
Stigmas: Color—Chartreuse Yellow, Plate 31.
Ovaries: All enclosed in calyx.
Hips: None.
Seeds: None.

*Plant*

Form: Bush.
Growth: Vigorous; dwarf.
Foliage: Compound of 3 to 7 leaflets.
*Size.*—Small.
*Quantity.*—Abundant.
*Color.*—New foliage: upper side—Oil Green, Plate 5; under side—Yellowish Oil Green, Plate 5. Old foliage: upper side—Elm Green, Plate 17; under side—Light Bice Green, Plate 17.

*Shape.*—Oval pointed.

*Texture.*—Upper side—leathery. Under side—smooth.

*Ribs and veins.*—Light.

*Edge.*—Serrated (saw-toothed).

*Serration.*—Single; small.

*Leaf stem.*—Color—Bice Green, Plate 17. Under side—smooth.

*Stipules.*—Short; bearded.

Wood:

*New wood.*—Color—Oil Green, Plate 5. Bark—smooth.

*Old wood.*—Color—Varley's Green, Plate 18. Bark—smooth.

Thorns:

*Thorns.*—Quantity: on main stalks from base—few; on laterals from stalk—few. Form—narrow base; short; hooked upward. Color (when young)—Chrysolite Green, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the miniature class, substantially as herein shown and described, characterized particularly as to novelty by the unique combination of a miniature plant and flower size, a flowering formation similar to that of the parent variety "Cecile Brunner" (unpatented), with three or four buds being borne together, a distinctive Venetian Pink shading of the buds, and a distinctive La France Pink general color tonality of the flowers.

No references cited.